US007955609B2

(12) United States Patent
Baron et al.

(10) Patent No.: US 7,955,609 B2
(45) Date of Patent: Jun. 7, 2011

(54) ACTIVE AGENT COMBINATIONS

(75) Inventors: Gerhard Baron, Leverkusen (DE); Michael Kilian, Leverkusen (DE); Frank Rosenfeldt, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 565 days.

(21) Appl. No.: 10/432,979

(22) PCT Filed: Nov. 19, 2001

(86) PCT No.: PCT/EP01/13340
§ 371 (c)(1),
(2), (4) Date: Oct. 3, 2003

(87) PCT Pub. No.: WO02/43496
PCT Pub. Date: Jun. 6, 2002

(65) Prior Publication Data
US 2004/0052878 A1 Mar. 18, 2004

(30) Foreign Application Priority Data
Dec. 1, 2000 (DE) .................................. 100 59 606

(51) Int. Cl.
*A01N 25/02* (2006.01)
(52) U.S. Cl. ........ 424/405; 424/406; 424/761; 514/341; 514/342; 514/450
(58) Field of Classification Search .................. 514/341; 424/407
See application file for complete search history.

(56) References Cited

U.S. PATENT DOCUMENTS

| | | | |
|---|---|---|---|
| 4,310,519 A | 1/1982 | Albers-Schonberg et al. | 424/181 |
| 4,329,518 A | 5/1982 | Plummer | 568/807 |
| 4,402,973 A | 9/1983 | Plummer | 424/305 |
| 4,429,042 A | 1/1984 | Albers-Schonberg et al. | 435/119 |
| 4,536,591 A | 8/1985 | Plummer | 560/8 |
| 4,623,658 A | 11/1986 | Anderson | 514/482 |
| 4,666,942 A | 5/1987 | Anderson | 514/594 |
| 4,668,792 A | 5/1987 | Plummer | 546/343 |
| 4,672,139 A | 6/1987 | Anderson | 560/16 |
| 4,849,432 A | 7/1989 | Shiokawa et al. | 514/341 |
| 5,034,404 A | 7/1991 | Uneme et al. | 514/365 |
| 5,262,383 A | 11/1993 | Fischer et al. | 504/195 |
| 5,367,093 A | 11/1994 | Dekeyser et al. | 560/27 |
| 5,438,123 A | 8/1995 | Dekeyser et al. | 534/885 |
| 5,472,700 A * | 12/1995 | Staetz et al. | 424/405 |
| 5,489,603 A | 2/1996 | Uneme et al. | 514/365 |
| 5,536,746 A | 7/1996 | Dekeyser et al. | 514/468 |
| 5,633,375 A | 5/1997 | Uneme et al. | 544/336 |
| 5,707,638 A * | 1/1998 | Losel et al. | 424/407 |
| 5,783,203 A * | 7/1998 | Schutte et al. | 424/405 |
| 5,939,441 A * | 8/1999 | Stetter et al. | 514/341 |
| 6,022,871 A | 2/2000 | Maienfisch et al. | 514/229.2 |

FOREIGN PATENT DOCUMENTS

| | | |
|---|---|---|
| CA | 2338361 | 2/2000 |
| DE | 44 26 942 A1 | 2/1996 |
| DE | 4426942 * | 2/1996 |
| DE | 19807630 * | 8/1999 |
| WO | 96/39034 | 12/1996 |

OTHER PUBLICATIONS

Chu et al, Arthropod Management Tests, p. 221, 1994.*
Riley Insecticide Control of Weetpotatoe Whitefly—Subtrop;ICAL Plant Science 46: 45-49, 1994.*
Koppenhofer A M, et al—Interactions of a Nucleopolyhedrovirus with Azadirachtin & Imidacloprid J. of Invertebrate Pathology Jan. 2000, vol. 75 # 1, pp. 84-86.*
The Pesticide Manual, 11th edition, British Corp. Protection Council, (month unavailable) 1997, No. 561, "permethrin", pp. 944-946.
The Pesticide Manual, 11th edition, British Corp. Protection Council, (month unavailable) 1997, No. 622, "pyrethrins", pp. 1056-1059.
The Pesticide Manual, 11th edition, British Corp. Protection Council, (month unavailable) 1997, No. 312, "fenpropathrin", pp. 524-525.
The Pesticide Manual, 11th edition, British Corp. Protection Council, (month unavailable) 1997, No. 176, "cyfluthrin", pp. 293-295.
The Pesticide Manual, 11th edition, British Corp. Protection Council, (month unavailable) 1997, No. 177, "beta-cyfluthrin", pp. 295-297.
The Pesticide Manual, 11th edition, British Corp. Protection Council, (month unavailable) 1997, No. 180, lambda-cyhalothrin, pp. 300-302.
The Pesticide Manual, 11th edition, British Corp. Protection Council, (month unavailable) 1997, No. 95, "butocarboxim", pp. 162-163.
The Pesticide Manual, 11th edition, British Corp. Protection Council, (month unavailable) 1997, No. 583, "primicarb", pp. 985-986.
The Pesticide Manual, 11th edition, British Corp. Protection Council, (month unavailable) 1997, No. 610, "propoxur", pp. 1036-1037.
The Pesticide Manual, 11th edition, British Corp. Protection Council, (month unavailable) 1997, No. 482, "methiocarb", pp. 813-815.
The Pesticide Manual, 11th edition, British Corp. Protection Council, (month unavailable) 1997, No. 429, "isazophos", pp. 726-727.
The Pesticide Manual, 11th edition, British Corp. Protection Council, (month unavailable) 1997, No. 243, "dimethoate", pp. 414-416.
The Pesticide Manual, 11th edition, British Corp. Protection Council, (month unavailable) 1997, No. 418, imidacloprid, pp. 706-707.
The Pesticide Manual, 11th edition, British Corp. Protection Council, (month unavailable) 1997, No. 5, "acetamiprid", pp. 9-10.
The Pesticide Manual, 11th edition, British Corp. Protection Council, (month unavailable) 1997, No. 1, "abamectin" pp. 3-5.
The Pesticide Manual, 11th edition, British Corp. Protection Council, (month unavailable) 1997, No. 231, diflubenzuron, pp. 395-397.
The Pesticide Manual, 11th edition, British Corp. Protection Council, (month unavailable) 1997, No. 92, "buprofexin", pp. 157-158.
The Pesticide Manual, 11th edition, British Corp. Protection Council, (month unavailable) 1997, No. 739, "triflumuron", pp. 1246-1248.
The Pesticide Manual, 11th edition, British Corp. Protection Council, (month unavailable) 1997, No. 208, "diafenthiuron", pp. 352-354.
The Pesticide Manual, 11th edition, British Corp. Protection Council, (month unavailable) 1997, No. 323, "fipronil", pp. 545-547.

(Continued)

*Primary Examiner* — Neil Levy
(74) *Attorney, Agent, or Firm* — Richard E. L. Henderson

(57) ABSTRACT

The invention relates to novel active compound combinations of extracts from seeds of the neem tree and the active compounds of groups (B) to (F) listed in the disclosure that have very good insecticidal and acaricidal properties.

3 Claims, No Drawings

OTHER PUBLICATIONS

The Pesticide Manual, 11th edition, British Corp. Protection Council, (month unavailable) 1997, No. 754, "XDE-105-spinosad", pp. 1272-1273.

The Pesticide Manual, 11th edition, British Corp. Protection Council, (month unavailable) 1997, No. 615, "pymetrozine", pp. 1045-1046.

The Pesticide Manual, 11th edition, British Corp. Protection Council, (month unavailable) 1997, No. 191, "cyromazine", pp. 321-322.

The Pesticide Manual, 11th edition, British Corp. Protection Council, (month unavailable) 1997, No. 224, "dicyclanil", p. 384.

The Pesticide Manual, 11th edition, British Corp. Protection Council, (month unavailable) 1997, No. 193, "D2341-bifenazate" pp. 327-329.

The Pesticide Manual, 11th edition, British Corp. Protection Council, (month unavailable) 1997, No. 401, "hexythiazox", pp. 679-680.

The Pesticide Manual, 11th edition, British Corp. Protection Council, (month unavailable) 1997, No. 680, "tebufenpyrad", pp. 1148-1150.

The Pesticide Manual, 11th edition, British Corp. Protection Council, (month unavailable) 1997, No. 624, "pyridaben", pp. 1061-1062.

* cited by examiner

ACTIVE AGENT COMBINATIONS

The present invention relates to novel active compound combinations which comprise, firstly, known extracts from seeds of the neem tree and, secondly, further known pesticidally active compounds, and which have very good insecticidal and acaricidal properties.

It is already known that extracts from the seeds of the neem tree have insecticidal properties (cf. "Römpp Chemie Lexikon", 9$^{th}$ edition, page 2954, Georg Thieme Verlag, Stuttgart—New York, 1991). The activity of this substance is good; however, it is sometimes unsatisfactory at low application rates.

It is furthermore known that numerous pyrethroids, carbamates, phosphoric acid derivatives and heterocycles can be used for controlling animal pests such as insects and undesirable acarids (cf. WO 93-10 083; DE-A 2 717 040; Farm Chemicals Handbook 1998, C 328; EP-A 0 161 019 and EP-A 0 049 977). However, the activity of these substances is likewise not always satisfactory at low application rates.

It has now been found that the novel active compound combinations comprising
A) extracts from seeds of the neem tree
and
B) an active compound from the group of the pyrethroids, consisting of
  (1) cypermethrin,
  (2) deltamethrin,
  (3) permethrin,
  (4) natural pyrethrum,
  (5) fenpropathrin,
  (6) cyfluthrin,
  (7) beta-cyfluthrin and
  (8) lambda-cyhalothrin,
or
C) an active compound from the group of the carbamates, consisting of
  (9) butocarboxim,
  (10) pirimicarb,
  (11) propoxur and
  (12) methiocarb,
or
D) a phosphoric acid derivative from the group consisting of
  (13) isazophos and
  (14) dimethoate,
(E) an active compound from the group of the nicotinyls or neonicotinyls consisting of
  (15) imidacloprid,
  (16) thiacloprid,
  (17) thiamethoxam,
  (18) acetamiprid and
  (19) clothianidin,
or
(F) an active compound from the group consisting of
  (20) abamectin,
  (21) diflubenzuron,
  (22) buprofezin,
  (23) triflumuron,
  (24) diafenthiuron,
  (25) fipronil,
  (26) spinosad,
  (27) pymetrozine,
  (28) cyromazine,
  (29) dicyclanil,
  (30) bifenazate,
  (31) hexathiazox,
  (32) tebufenpyrad,
  (33) pyridaben,
  (34) the ketoenol derivative (I) of the name 3-(2,4-dichlorophenyl)-4-(1,1-dimethyl-propyl-carbonyloxy)-5-spiro-cyclohexyl-3-dihydrofuran-2-one
  and
  (35) the ketoenol derivative (II) of the name 3-(2,4,6-trimethylphenyl)-4-(2,2-dimethyl-propyl-carbonyloxy)-5-spiro-cyclopentyl-3-dihydrofuran-2-one
have very good insecticidal and acaricidal properties.

Surprisingly, the insecticidal and acaricidal activity of the active compound combinations according to the invention is considerably higher than the sum of the activities of the individual active compounds. Thus, an unforeseeable, true synergistic effect is present, and not just an addition of activities.

In the present case, extracts from seeds of the neem tree are to be understood as meaning all customary products which can be isolated from seeds of the neem tree by extraction or squeezing and which contain substantial quantities of azadirachtin. These products include azadirachtin itself.

Various extracts of seeds of the neem tree and azadirachtin itself are already known (cf. "The Pesticide Manual" 11$^{th}$ edition, British Crop Protection Council 1997, No. 36 and also "Römpp Chemie Lexikon", 9$^{th}$ edition, page 2954, Georg Thieme Verlag, Stuttgart—New York, 1991).

The insecticidally and acaricidally active components which are present in the active compound combinations according to the invention in addition to the extracts from the seeds of the neem tree are likewise known. The following substances are specifically described in "The Pesticide Manual", 11$^{th}$ edition, British Crop Protection Council, 1997:

| (1) | cypermethrin | under No. 185, |
|---|---|---|
| (2) | deltamethrin | under No. 204, |
| (3) | permethrin | under No. 561, |
| (4) | natural pyrethrum | under No. 622, |
| (5) | fenpropathrin | under No. 312, |
| (6) | cyfluthrin | under No. 176, |
| (7) | beta-cyfluthrin | under No. 177, |
| (8) | lambda-cyhalothrin | under No. 180 |
| (9) | butocarboxim | under No. 95, |
| (10) | pirimicarb | under No. 583, |
| (11) | propoxur | under No. 610, |
| (12) | methiocarb | under No. 482, |
| (13) | isazophos | under No. 429, |
| (14) | dimethoate | under No. 243, |
| (15) | imidacloprid | under No. 418, |
| (18) | acetamiprid | under No. 5, |
| (20) | abamectin | under No. 1, |
| (21) | diflubenzuron | under No. 231, |
| (22) | buprofezin | under No. 92, |
| (23) | triflumuron | under No. 739, |
| (24) | diafenthiuron | under No. 208, |
| (25) | fipronil | under No. 323, |
| (26) | spinosad | under No. 754, |
| (27) | pymetrozine | under No. 615 |
| (28) | cyromazine | under No. 191, |
| (29) | dicyclanil | under No. 244, |
| (30) | bifenazate | under No. 193, |
| (31) | hexathiazox | under No. 401, |
| (32) | tebufenpyrad | under No. 680 and |
| (33) | pyridaben | under No. 624. |

The other of the above-mentioned active compounds are described in the following publications:

| (16) thiacloprid | EP-A-0 235 725 |
|---|---|
| (17) thiamethoxam | EP-A 0 580 553, |

-continued

| (19) clothianidin | EP-A 0 376 279, |
| (34) ketoenol derivative (I) | EP-A 0 528 156 and |
| (35) ketoenol derivative (II) | EP-A 0 528 156. |

In addition to the extract from the seeds of the neem tree, the active compound combinations according to the invention comprise at least one of the active compounds from groups (B) to (F). Additionally, they may comprise further insecticidally and/or acaricidally active components.

The synergistic effect is particularly pronounced if the active compounds are present in the active compound combinations according to the invention in certain weight ratios. However, the weight ratios of the active compounds in the active compound combinations can be varied within a relatively wide range. In general,
from 0.02 to 20 parts by weight, preferably from 0.3 to 17 parts by weight, of active compound from group (B),
from 1 to 80 parts by weight, preferably from 1.5 to 70 parts by weight, of active compound from group (C),
from 1 to 60 parts by weight, preferably from 3 to 50 parts by weight, of active compound from group (D),
from 0.2 to 50 parts by weight, preferably from 0.3 to 40 parts by weight, of active compound from group (E) and
from 0.2 to 60 parts by weight, preferably from 0.3 to 50 parts by weight, of active compound from group (F)
are present per part by weight of extract from seeds of the neem tree.

The active compound combinations according to the invention are suitable for controlling animal pests, preferably arthropods and nematodes, in particular insects and arachnids, which are encountered in agriculture, in gardening, in forests, in the protection of stored products and of materials and in the hygiene sector. They are active against normally sensitive and resistant species and also against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Blattaria, for example, *Blatta orientalis, Periplaneta americana, Leucophaea maderae* and *Blattella germanica.*

From the order of the Orthoptera, for example, *Acheta domesticus, Gryllotalpa* spp., *Locusta migratoria migratorioides, Melanoplus differentialis* and *Schistocerca gregaria.*

From the order of the Dermaptera, for example, *Forficula auricularia.*

From the order of the Isoptera, for example, *Reticulitermes* spp.

From the order of the Anoplura, for example, *Phylloxera vastatrix, Pemphigus* spp., *Pediculus humanus corporis, Haematopinus* spp. and *Linognathus* spp.

From the order of the Mallophaga, for example, *Trichodectes* spp. and *Damalinea* spp.

From the order of the Thysanoptera, for example, *Frankliniella occidentalis, Hercinothrips femoralis, Thrips palmi* and *Thrips tabaci.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporarionirm, Aphis gossypii, Brevicoryne brassicae, Cryptomyzus ribis, Aphis fabae, Doralis pomi, Eriosoma lanigenirm, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Spodoptera exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Lyriomyza* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa.*

From the order of the Siphonaptera, for example, *Xenopsylla cheopis* and *Ceratophyllus* spp.

From the order of the Arachnida, for example, *Scorpio maurus* and *Latrodectus mactans.*

From the order of the Acarina, for example, *Acarus siro,* Argas spp., *Omithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

The active compound combinations according to the invention can be used with particularly good results for controlling plant-damaging insects and acarids, such as, for example, against *Tetranychus* spp., *Panonychu* spp., *Hemi-*

*tarsonemus* spp., *Tarsonemus* spp., *Brevipalpus* spp., *Phylocoptruta* spp., *Aculus* spp., *Bryobia* spp. and *Eriophyes* spp.

The fact that the active compound combinations are well tolerated by plants at the concentrations required for controlling insects and acarids permits the treatment of above-ground parts of plants, of propagation stock and seeds, and of the soil. The active compound combinations according to the invention can be used for foliar application or else as seed dressing.

The active compound combinations according to the invention are usually employed in the form of compositions (formulations), for the preparation of which it is possible to use the extracts from the seeds of the neem tree in a commercial preparation or in the form of isolated substances and the active compounds of groups (B) to (F) either as such or in commercial preparations.

The active compound combinations according to the invention can be converted into the customary compositions (formulations), such as solutions, emulsions, suspensions, powders, foams, pastes, granules, aerosols, microencapsulations in polymeric compounds and in coating compositions for seeds, and ULV formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Essentially, suitable liquid solvents include aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane, or paraffins, for example petroleum fractions, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers refer to those liquids which are gaseous at normal temperature and under atmospheric pressure, for example aerosol propellants, such as butane, propane, nitrogen and carbon dioxide. Suitable solid carriers are: for example ground natural minerals, such as kaolins, clays, talc, chalk, quartz, attapulgite, montmorillonite or diatomaceous earth, and ground synthetic minerals, such as finely divided silica, alumina and silicates. Suitable solid carriers for granules are: for example crushed and fractionated natural rocks, such as calcite, marble, pumice, sepiolite and dolomite, or else synthetic granules of inorganic and organic meals, and granules of organic materials such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers, such as carboxymethylcellulose and natural and synthetic polymers, in the form of powders, granules or latices, such as gum arabic, polyvinyl alcohol and polyvinyl acetate, or else natural phospholipids, such as cephalins and lecithins and synthetic phospholipids, can be used in the formulations. Other possible additives are mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 percent by weight of active compounds, preferably between 0.5 and 90%.

In the formulations, the active compound combinations according to the invention can be present as a mixture with other known active compounds, such as fungicides, insecticides, acaricides and herbicides, and as mixtures with fertilizers or plant growth regulators chelates or superabsorbers.

The active compound combinations can be employed as such, in the form of their formulations or of the use forms prepared therefrom, such as ready-to-use solutions, emulsifiable concentrates, emulsions, suspensions, wettable powders, soluble powders, granules and shaped articles. The application is carried out in a customary manner, for example by watering, spraying, atomizing, scattering, spreading, dry dressing, wet dressing, liquid dressing, slurry treatment of seeds, incrustation, implantation, injection or by foam application.

When using the active compound combinations according to the invention, the application rates can be varied within a relatively wide range, depending on the type of application. In the treatment of parts of plants, the application rates of active compound combinations are generally between 10 and 3000 g/ha, preferably between 20 and 2000 g/ha.

In the treatment of the soil, the application rates of active compound combinations are generally between 10 and 4000 g/ha, preferably between 20 and 2000 g/ha.

In the treatment of seeds, the application rates are generally between 0.01 and 50 g/kilogram of seed, preferably between 0.05 and 40 g/kilogram of seed.

The good insecticidal and acaricidal activity of the active compound combinations according to the invention is demonstrated by the examples below. Whereas the individual active compounds have weaknesses in the activity, the combinations have an activity which exceeds a simple addition of activities.

A synergistic effect of insecticides and acaricides is therefore always present when the activity of the active compound combinations exceeds the total of the activities of the active compounds when applied individually.

The expected activity for a given combination of two active compounds can be calculated according to S. R. Colby, Weeds 15 (1967), 20-22), as follows:

If

X is the efficacy when applying the active compound A at an application rate of m g/ha, Y is the efficacy when applying the active compound B at an application rate of n g/ha and E is the efficacy when applying the active compounds A and B at application rates of m and n g/ha, then $$E = X + Y - \frac{X \cdot Y}{100}.$$

Here, the efficacy is determined in %. 0% means an efficacy which corresponds to that of the control, whereas an efficacy of 100% means that no infection is observed.

If the actual activity exceeds the calculated value, then the activity of the combination is superadditive, i.e. a synergistic effect exists. In this case, the efficacy which was actually observed must be greater than the value for the expected efficacy (E) calculated from the formula given above.

The invention is illustrated by the following examples:

EXAMPLE 1

Trialeurodes Test

To produce a suitable preparation of active compound, a commercial formulation of active compound or active compound combination is mixed with water until the desired concentration is reached.

Red sage (*Lantana camara*) which is heavily infested by all stages of the whitefly (*Trialeurodes vaporariorum*) is sprayed in intervals of 7 days in each case with a preparation of active compound at the desired application rate.

Evaluation is carried out 15 days after the second treatment. 100% means that all flies have been killed, whilst 0% means that none of the flies have been killed.

Active compounds, application rates and test results are shown in the table below.

TABLE 1

| | Trialeurodes test | |
|---|---|---|
| Active compound | Application rate of active compound in g/ha | Kill rate in % |
| Known: | | |
| Neem extract*) | 30 | 28.6 |
| (16) thiacloprid | 100 | 72.8 |
| According to the invention | | found calc.**) |
| | | 91.9 80.6 |
| Neem extract*) + (16) Thiacloprid | 30 + 100 | |

*)The neem tree seed extract used is commercially available under the name Neem-Azal ® (from Terfolio).
**)found = activity found
calc. = activity calculated using Colby's formula

EXAMPLE 2

Trialeurodes Test

To produce a suitable preparation of active compound, a commercial formulation of active compound or active compound combination is mixed with water until the desired concentration is reached.

Red sage (*Lantana camara*) which is heavily infested by the whitefly (*Trialeurodes vaporariorum*) is sprayed in intervals of 7 days in each case with a preparation of active compound at the desired application rate.

Evaluation is carried out 15, 19 and 25 days after the second treatment. 100% means that all flies have been killed, whilst 0% means that none of the flies have been killed.

Active compounds, application rates and test results are shown in the table below.

TABLE 2

| | Trialeurodes test | | | |
|---|---|---|---|---|
| Active compound | Application rate of active compound in g/ha | Kill rate in % 15 days after the second treatment | Kill rate in % 19 days after the second treatment | Kill rate in % 25 days after the second treatment |
| Known: | | | | |
| Neem extract*) | 30 | 28.6 | 0 | 0 |
| (16) Thiacloprid | 100 | 72.8 | 39.5 | 0 |
| According to the invention | | found calc.) | found calc.) | found calc.**) |
| Neem extract*) + (16) Thiacloprid | 30 + 100 | 91.9 80.6 | 82.7 39.5 | 70.0 0 |

*)The neem tree seed extract used is commercially available under the name Neem-Azal ® (from Trifolio).
**)found = activity found
calc. = activity calculated using Colby's formula

What is claimed is:

1. An insecticidal and acaricidal composition comprising an active compound combination consisting essentially of (A) extracts from seeds of the neem tree, and
   (B) at least one active compound selected from the group of nicotinoyls and neonicotinyls consisting of
      (1) imidacloprid, and
      (2) thiacloprid, wherein the weight ratio of the extract from seeds of the neem tree of component (A) to the active compound of component (B) is from 1:0.2 to 1:50,
   and one or more extenders and/or surfactants.

2. A method for controlling insects or acarids comprising applying an effective amount of an active compound combination as claimed in claim 1 to insects or acarids and/or to the habitats of the insects or acarids.

3. A process for preparing an insecticidal or acaricidal composition comprising mixing an active compound combination as claimed in claim 1 with one or more extenders and/or surfactants.

* * * * *